United States Patent [19]

Hill

[11] Patent Number: 5,368,481

[45] Date of Patent: Nov. 29, 1994

[54] DENTAL MOLD APPARATUS

[76] Inventor: Steven J. Hill, 3906 Sunnycrest Drive, North Vancouver, British Columbia, Canada, V7R 3C9

[21] Appl. No.: 90,259

[22] Filed: Jul. 13, 1993

[51] Int. Cl.⁵ .................................. A61C 3/14
[52] U.S. Cl. ........................... 433/159; 433/34
[58] Field of Search ............... 433/34, 39, 156, 159, 433/229; 249/54; 264/16

[56] References Cited

U.S. PATENT DOCUMENTS

| 512,840 | 1/1894 | Phelpe | 249/54 |
|---|---|---|---|
| 600,604 | 3/1898 | Baird | 433/159 |
| 1,265,581 | 5/1918 | Zurbrigg | 433/39 |
| 2,267,836 | 12/1941 | Parkin | 433/39 |

*Primary Examiner*—Cary E. O'Connor

[57] ABSTRACT

A novel hand-held pressure molding device about the size of a pair of pliers is used to produce a contoured matrix of dental restorative composite resin for use in restoring teeth to their approximate original shape. The matrix produced by the device is bonded in place to establish the old contour of the tooth and then the space between the tooth and the matrix is filled with uncured dental restorative composite. After curing by actinic light, the matrix bonds to the rest of the filling and the tooth, forming the outside contour of the restored tooth. The present device avoids the need for supplying preformed and pre-shaped dental matrices in multiple shapes and sizes to the dental practitioner, allowing the practitioner to manufacture his matrices in his office from the identical material subsequently used to fill a tooth.

6 Claims, 3 Drawing Sheets

U.S. Patent    Nov. 29, 1994    5,368,481
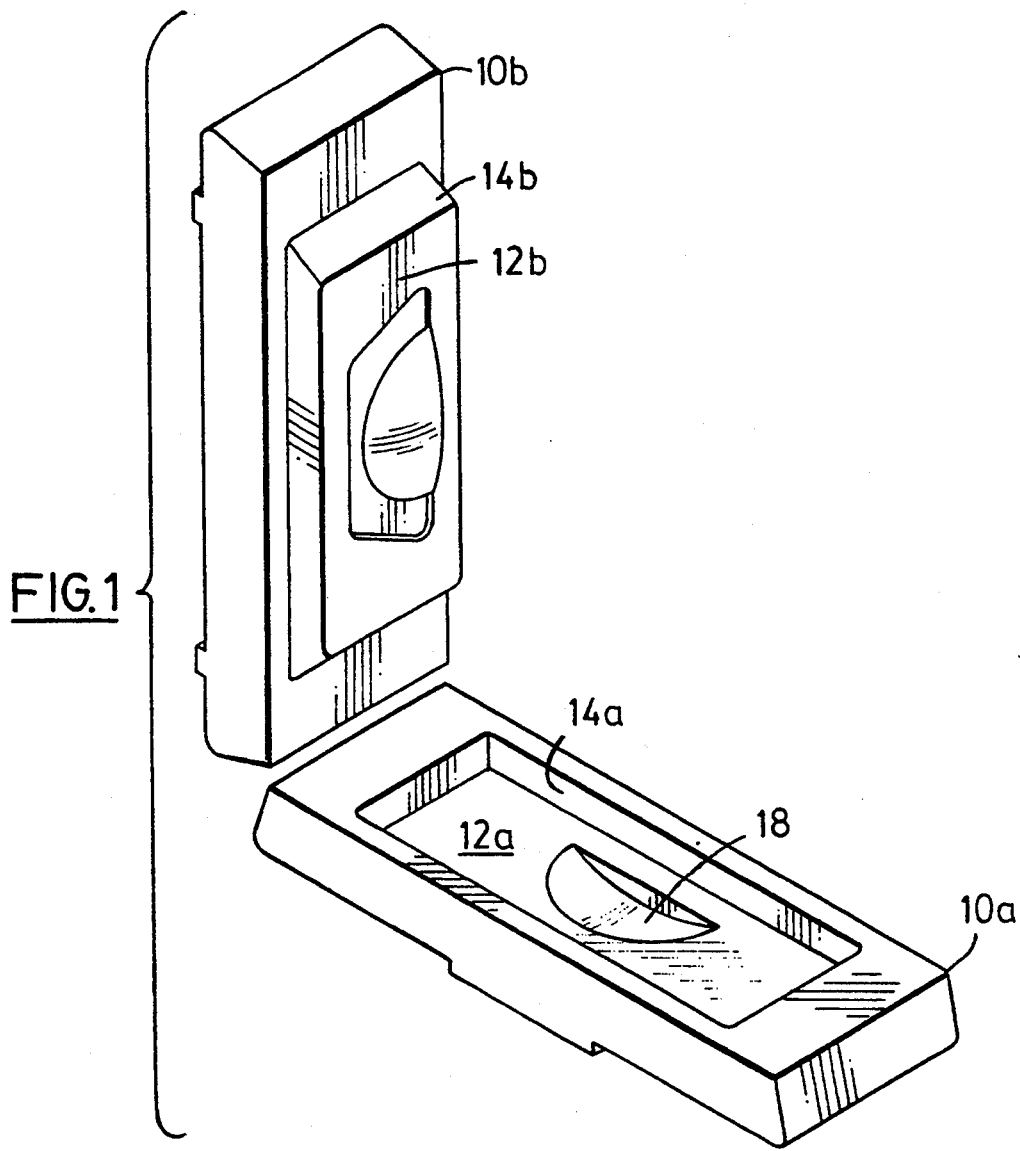
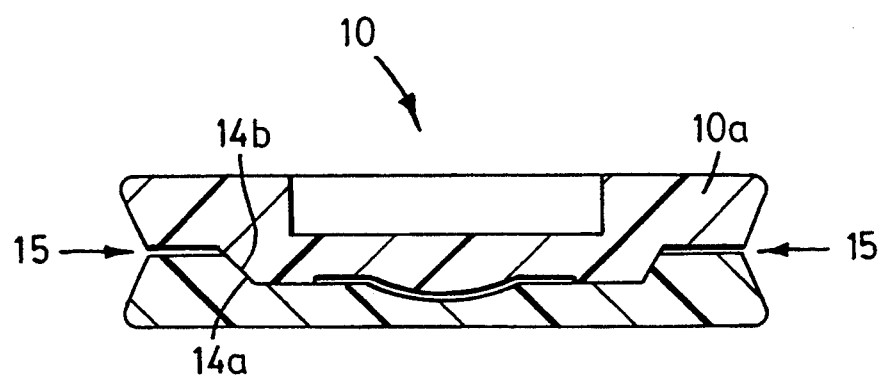

DENTAL MOLD APPARATUS

BACKGROUND OF THE INVENTION

1. Field of the Invention

This invention relates to the preparation of dental matrix bands from composite dental resins and, more specifically, to a manual pressure molding device which may be used by a dentist in his office to prepare dental matrices in a variety of selected contours for use in restoring teeth to their approximate original shape.

2. Description of the Prior Art

The advantages possessed by composite dental resins over dental amalgam alloys in the restoration ("filling") of teeth have led to increasing acceptance of the former. These advantages include color matching and smoothness, and bondability.

A known and widely-used restoration procedure employing composite fillings involves the removal of decayed material from a tooth, wrapping a matrix band around the tooth to define the volume which will contain the composite restoration material, inserting a wedge between the outer surface of the band and the adjacent tooth, placing the composite restoration material in the void and curing it to hardness, usually by irradiation with a source of actinic light, then removing the matrix band and wedge.

It has been recognized that removal of the matrix band in an interproximal restoration carried out by the foregoing procedure often results in the formation of an undesirable "open contact", in which the filling of the restored tooth and the surface of the adjacent tooth do not abut, but present a gap between them.

A number of procedures and devices have been developed with a view to reducing the number of open contacts in dental restoration. With composite filling materials, a recent approach to the problem has been to employ non-removable matrices, made of the same composite material as the filling or of a similar material bondable to the restored tooth and composite filling. Unlike conventional, removable and non-bondable matrix bands made of stainless steel or Mylar (TM), the non-removable matrix band or a portion of it remains in place after the resin-based filling is cured.

An example of this approach (i.e. non-removable composite matrix) is disclosed in U.S. Pat. No. 4,778,385 (Herrin) directed to a matrix having a concave inner surface for adhesion to a posterior tooth in restoration, made of the same material as the composite restoration. However, being pre-formed, pre-shaped and non-flexible, these matrices must be supplied to the dentist in a variety of forms. A matrix of the appropriate size and contour to cover the proximal cavity and to prevent a gap between the restoration and the adjacent tooth is put firmly in place with the assistance of a subsequently-removed wedge. The requirement for an inventory of variously shaped matrices is costly and inconvenient.

U.S. Pat. No. 5,035,615 (Din) discloses the use of a flexible, rectangular matrix band of composite material to generate the outside of the tooth being restored. The band may be formed by mixing a conventional light-activated filler material with a conventional light-cured liquid resin, drawing the mixture into a film and finally curing the film of which the matrix band is made. The flexible composite matrix band so produced is held firmly against the tooth being restored, passively abutting an adjacent tooth. A bonding agent is applied to the surface of the prepared cavity in the tooth and to the matrix band. After curing of the bonding agent the cavity is filled with a composite resin which is then cured, followed by removal by the dentist of unbonded portions of the matrix band.

Although thin and flexible, the matrix band of Din has no contour to adjust well to the outer contoured surface of the restored tooth. Placement of a contoured matrix which closely matches the shape of the tooth surface, after treating the tooth surface with a bonding agent, seals the matrix to the tooth. As the matrix is already fully cured, it does not shrink during the curing cycle of the restorative material, avoiding the formation of any gap between the bottom edge of the prepared cavity and the final restoration.

SUMMARY OF THE INVENTION

It is an object of the present invention to provide a simple, hand-held device for use by dental practitioners or their assistants to prepare a contoured dental matrix for permanent bonding to the filling and the tooth in a composite dental restoration.

It is a further object of the invention to provide a device as aforesaid, including interchangeable molds transparent to actinic light for preparing contoured dental matrices from composite material in a variety of selected contours adapted for bonding to differently contoured teeth.

BRIEF DESCRIPTION OF THE DRAWINGS

Various features of the invention will be apparent from the description which follows and from the drawings, in which:

FIG. 1 is a perspective view of the two compression mold halves used in the device of the present invention;

FIG. 2 is a sectional view of the compression mold used in the apparatus of the invention, with the two halves of FIG. 1 juxtaposed in closed configuration;

DESCRIPTION OF THE PREFERRED EMBODIMENT

The pressure molding device according to the present invention comprises a two-piece compression mold made of a material transparent to actinic light and a pliers-like gripping device for urging the two halves of the mold together to form uncured composite resin put in the mold into the shape of dental matrix desired and for holding the assembled mold and resin in exposure to a beam of resin-curing light. A particularly advantageous material for the molds is the polymethylpentene plastic sold by Mitsui Petrochemical Industries Ltd. (Japan) under the trade mark TPX, which exhibits both the necessary degree of light transparency and low adhesion to cured composite resins of the kind from which dental matrices are made by the present method.

Figure 2A:
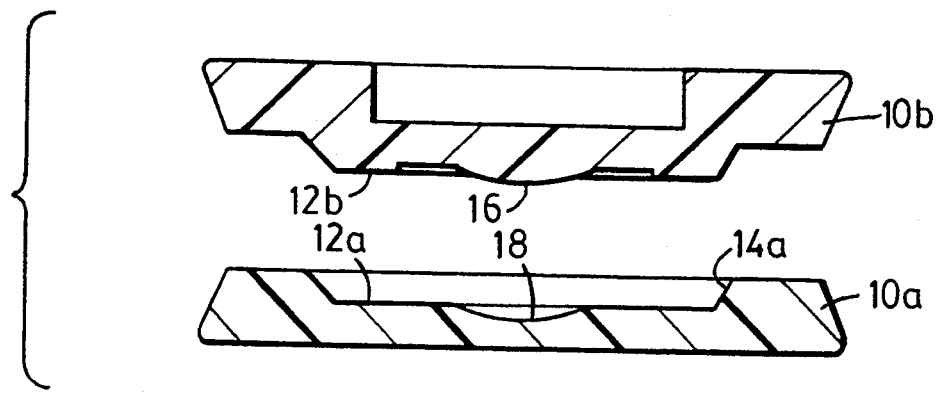
FIG. 2A is a sectional view of the compression mold used in the apparatus of the invention, with the two halves of FIG. 1 superposed and vertically spaced apart.

As best seen in FIGS. 1, 2 and 2A, the compression mold 10 consists of a female mold section 10a and a male mold section 10b. To receive the flowable, uncured composite which will form the dental matrix, mold section 10a includes a rectangular well bounded by recessed surface 12a and bevelled, four-sided edge formation 14a. The corresponding outwardly stepped surface and bevelled edge formation of mating mold section 10b are indicated as 12b and 14b, respectively.

When mold sections 10a and 10b are pressed matingly together as assembled in FIG. 2, surfaces 12a and 12b are brought together and edge formation 14b fits closely against and circumscribed by edge formation 14a, so that excess composite is squeezed out of the mold through a narrow peripheral space 15 between the mold sections.

Retained within the centre of the mold within perimetrically closed space 17 is a portion of uncured composite in the shape of the desired dental matrix. Cavity 17 is delineated when the mold sections are assembled by the mating of die portion 16 and die cavity 18.

Figure 5:
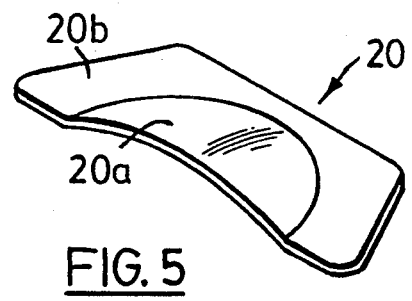
FIG. 5 is an enlarged perspective view of a contoured composite dental matrix produced by use of the device of the invention.

The die portion 16 and die cavity 18 in the embodiment of compression mold illustrated in FIGS. 1 and are configured to produce, after curing of the composite and separation of the mold sections, a dental matrix 20 having the shape illustrated in FIG. 5.

Dental matrix 20 is typically of a thickness about 0.1 mm and dimensions about 0.5×1.5 cm. The concave-convex curved portion 20a conforms to the removed surface contour of a tooth undergoing restoration, while integral "skirt" portion 20b enables the matrix to be handled, trimmed and inserted with conventional dental tools. As seen in FIG. 1, to form this particular shape of matrix, the portion 16a of die 16 corresponding to the skirt is made a flat surface recessed from the outwardly-stepped surface of the male mold section.

In using matrix 20, or a matrix of some other appropriate contour formed in a compression mold 10 having a differently shaped die portion and die cavity, the dentist forms a prepared cavity in the usual way. Matrix 20, which has been prepared using the pressure molding device as discussed below, is supported against the margins of the cavity with its outer surface passively abutting the adjacent tooth. A conventional bonding agent such as Scotch Bond Multipurpose (3M) is applied to secure the matrix to the tooth, restoring the tooth's original contour, and the prepared cavity is filled with a composite resin of the same composition as that used to make matrix 20. Typical conventional resins which are suitable for this purpose include APH (Caulk), Silex (3M) and Visar Seal (Denmet Corporation). The resin is cured by light and the skirt 20b of the matrix is cut away.

Figure 3:
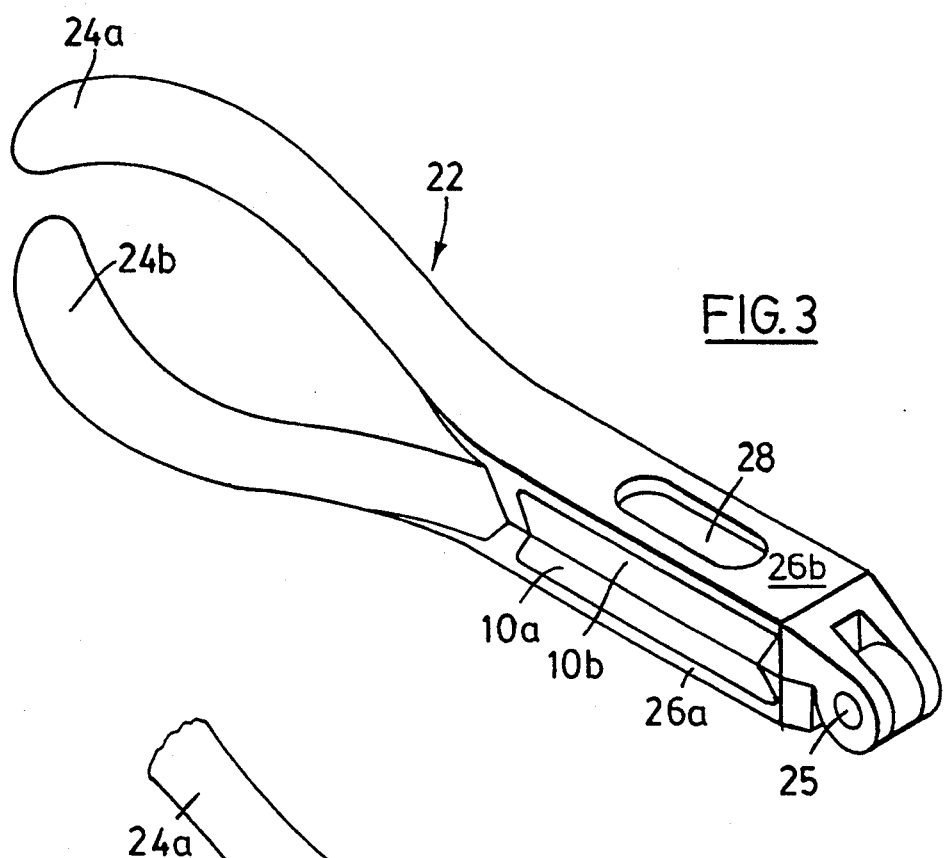
FIG. 3 is a perspective view of the compression mold holder used in the device of the invention, in the closed configuration.
Figure 4:
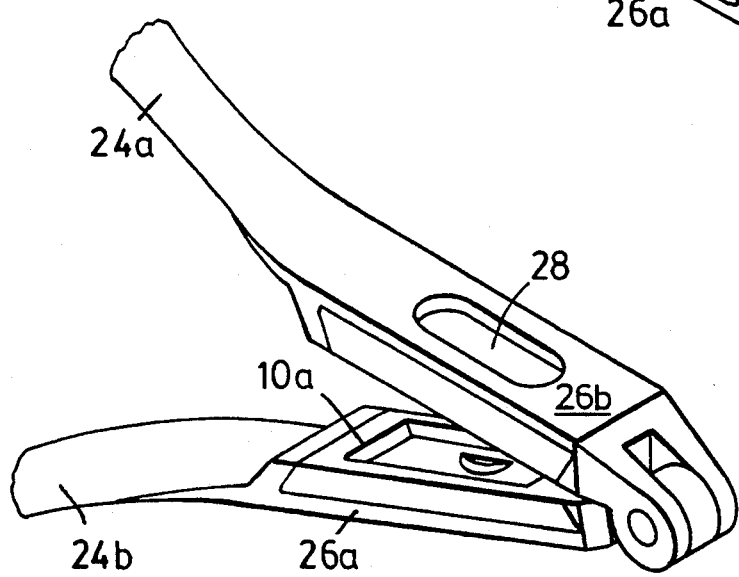
FIG. 4 is a partial perspective view of the compression mold holder used in the invention in the open configuration, including a compression mold half in its operative position received in the holder.

Illustrated in FIGS. 3 and 4 is the pliers-like gripping device which is used in association with compression mold 10. Handles 24a and 24b are pivotably linked at the front for rotation about pin 25. The front portion of each handle is provided with a mold section holder (26a, 26b) each having a transversely extending channel for slidably receiving and holding one of the mold sections against an outer bearing plate. In the illustrated embodiment, perpendicular separation of a mold section from the channel handle in which it is inserted is prevented by the front and rear walls of the channel being bevelled to engage similarly bevelled front and rear edge surfaces of the mold sections, as indicated at 27a and 27b.

In charging the pressure molding device illustrated, the practitioner will separate handles 24a and 24b by about 180° and install the male and female mold sections in the two holder channels. The uncured composite is injected into the well of female mold section 10a and the handle 24b of the holder carrying the male mold section is rotated back to bring it die-side down into mating juxtaposition with the female mold section. Manual pressure is exerted to shape the uncured composite between the die and die cavity as discussed above.

The bearing plates of the gripping means include superposed apertures 28 to permit light to irradiate the curing matrix, when the practitioner holds the gripped compression mold under a suitable source of actinic light, such as the Caulk MAX system. When curing is complete, the assembled mold is slid laterally free of the channels of the gripping device and the two mold sections are manually separated to free the formed matrix 20, which is then used in a dental restoration as described above.

Use of the pressure molding device of the present invention permits a dental practitioner to select for a matrix material any of a variety of composite filling materials in desired tooth-matching colours. By having a set of ten or so molds of various contours, an appropriate selection may be made to mitigate the problem of open contacts and of gaps arising from polymerization shrinkage at the margin of the tooth.

I claim:

1. A manually operable pressure molding device for preparing a composite dental matrix having a desired contour, comprising:
    a pressure mold fabricated of an actinic light-transparent material, comprising a female mold section for receiving a quantity of flowable, uncurred light-curable composite resin and a male mold section, said mold sections being so configured that pressing them matingly together into a limiting closed relationship retains a portion of said uncured resin within a perimetrically closed space defines the desired contour of dental matrix; and
    gripping means for holding the pressure mold and for applying pressure to urge said mold sections matingly together, comprising a pair of mold section holding portions pivotably interconnected at one end thereof and each having at the other end thereof an integral elongate handle, so configured that said mold sections held in respective holding portions are brought into mating juxtaposition when said handle members are pivoted together, said mold section holding portions including apertures to permit light from an external source of actinic light to irradiate said perimetrically closed cavity of said pressure mold held by the gripping means to cure said portion of resin into a dental matrix.

2. A device according to claim 1, wherein each of said mold section holding portions includes an outer bearing surface to bear against the outer wall of a respective mold section and includes a transversely extending recess for slidably receiving and holding its associated mold section against its bearing surface.

3. A device according to claim 2, wherein said apertures are centrally located on each of said bearing surfaces.

4. A device according to claim 2, wherein each of said mold section holding portions has bevelled side edges forming said transversely extending recess with said outer bearing surface and said mold sections have correspondingly bevelled side edges which engage said side edges of the mold sections to prevent perpendicular separation of a mold section from the mold section holding portion.

5. A device according to claim 1, wherein said desired contour of dental matrix comprises a convex curved central portion adapted to the original contour of a tooth to be restored and an integral flat skirt portion surrounding said central portion.

6. A device according to claim 5, wherein the thickness of said desired contour is about 1 mm.

* * * * *